US012121308B2

(12) United States Patent
Chang et al.

(10) Patent No.: US 12,121,308 B2
(45) Date of Patent: Oct. 22, 2024

(54) AUGMENTED REALITY SYSTEM FOR REAL SPACE NAVIGATION AND SURGICAL SYSTEM USING THE SAME

(71) Applicant: HES IP HOLDINGS, LLC, Austin, TX (US)

(72) Inventors: Yin Chang, Taipei (TW); Yung-Chin Hsiao, Taipei (TW); Jiunn-Yiing Lai, New Taipei (TW)

(73) Assignee: HES IP HOLDINGS, LLC, Austin, TX (US)

( * ) Notice: Subject to any disclaimer, the term of this patent is extended or adjusted under 35 U.S.C. 154(b) by 0 days.

(21) Appl. No.: 18/559,782

(22) PCT Filed: Aug. 1, 2022

(86) PCT No.: PCT/US2022/039080
§ 371 (c)(1),
(2) Date: Nov. 8, 2023

(87) PCT Pub. No.: WO2023/014667
PCT Pub. Date: Feb. 9, 2023

(65) Prior Publication Data
US 2024/0268896 A1    Aug. 15, 2024

Related U.S. Application Data

(60) Provisional application No. 63/228,171, filed on Aug. 2, 2021.

(51) Int. Cl.
*A61B 34/20*    (2016.01)
*A61B 17/34*    (2006.01)
(Continued)

(52) U.S. Cl.
CPC .......... *A61B 34/20* (2016.02); *A61B 17/3403* (2013.01); *A61B 34/25* (2016.02);
(Continued)

(58) Field of Classification Search
None
See application file for complete search history.

(56) References Cited

U.S. PATENT DOCUMENTS

2015/0248793 A1    9/2015  Abovitz et al.
2017/0004749 A1    1/2017  Deering et al.
(Continued)

FOREIGN PATENT DOCUMENTS

CN    105011900 A    11/2015
CN    110076277 A     8/2019
(Continued)

OTHER PUBLICATIONS

International Search Report in the related PCT application No. PCT/US2022/039080, dated Dec. 13, 2022.
IPRP in the related PCT application No. PCT/US2022/039080, dated Nov. 20, 2023.
(Continued)

*Primary Examiner* — Edward Martello
(74) *Attorney, Agent, or Firm* — Chen Yoshimura LLP

(57) ABSTRACT

The present disclosure relates to an augmented reality system for real space navigation. The augmented reality system comprises a navigation module for determining a set of spatial coordinates corresponding a position in a three dimensional real space for each of a plurality of navigation landmarks; and a virtual image display module for displaying a virtual image correlated to one of the plurality of navigation landmarks such that the virtual image is perceived by a user to be at the position in the three dimensional real space, the virtual image being composed of at least one binocular pixels, each of the binocular pixels is formed by a first light signal projecting to a first retina of the user and a second light signal projecting to a second retina of the user.

20 Claims, 12 Drawing Sheets

(51) Int. Cl.
*A61B 34/00* (2016.01)
*A61B 90/00* (2016.01)
*A61B 90/50* (2016.01)
*G06T 19/00* (2011.01)
*H04N 13/128* (2018.01)
*H04N 13/366* (2018.01)
*H04N 13/398* (2018.01)

(52) U.S. Cl.
CPC ......... *G06T 19/003* (2013.01); *H04N 13/128* (2018.05); *H04N 13/366* (2018.05); *H04N 13/398* (2018.05); *A61B 2090/363* (2016.02); *A61B 2090/365* (2016.02); *A61B 2090/502* (2016.02); *G06T 2210/41* (2013.01)

(56) References Cited

U.S. PATENT DOCUMENTS

| | | |
|---|---|---|
| 2017/0027651 A1 | 2/2017 | Esterberg |
| 2017/0115742 A1 | 4/2017 | Xing et al. |
| 2019/0137764 A1 | 5/2019 | Kang et al. |
| 2020/0081530 A1 | 3/2020 | Greenberg |
| 2021/0161600 A1* | 6/2021 | Heaney ................. A61B 90/37 |

FOREIGN PATENT DOCUMENTS

| | | |
|---|---|---|
| JP | 5476036 B2 | 4/2014 |
| TW | 201907204 A | 2/2019 |

OTHER PUBLICATIONS

Taiwanese Office Action, dated Jun. 29, 2023, in a counterpart Taiwanese patent application, No. TW 111128980.

* cited by examiner

| Virtual binocular Pixel | pair of designated location | Spatial coordinate (horizontal, vertical, depth) |
|---|---|---|
| BP1 | R(11), L(11) | h1, v1, d1 |
| BP2 | R(11), L(11) | h2, v2, d2 |
| ... | ... | ... |
| BP216 | R(66), L(66) | h216, v216, d216 |

AUGMENTED REALITY SYSTEM FOR REAL SPACE NAVIGATION AND SURGICAL SYSTEM USING THE SAME

RELATED APPLICATION

This application claims the priority of the provisional application 63/228,171 filed on Aug. 2, 2021, titled "A DEVICE AND METHOD WITH MIXED REALITY FOR GUIDING NEEDLE INSERTION".

FIELD OF THE INVENTION

The present invention relates to an augmented reality based navigation system; more particularly, an augmented reality based navigation system capable of displaying virtual images to guide a user to perform and complete a task. The present invention further relates to an augmented reality based navigation system for guiding a medical practitioner to perform and complete a medical procedure, such as surgery.

DESCRIPTION OF RELATED ART

In conventional practice, medical practitioners need to rely on medical record displayed on a computer screen as a reference for performing a medical procedure. The medical practitioners often need to look back and forth between the patient and the computer screen, which may be troublesome. Furthermore, the determination of the correct location and path for operating surgical instruments while performing the medical procedure often rely heavily on the experience of the medical practitioners. As an example, epidural needle insertion into the spinal area for epidural anesthesia requires precise insertion location and epidural needle orientation for preventing damage to the collateral tissues. Anesthetists often need to relay on ultrasonic imaging device for determining the location and orientation of insertion of the epidural needle. However, ultrasonic imaging device cannot be placed directly on the site of insertion; rather, it is placed on the side of the site of insertion, which undesirably limit the accuracy of the image and increase the probability of procedure failure.

Many augmented reality assisted medical procedures have been conceived in recent years. However, the technology regarding accurately mapping the location of a three dimensional virtual object perceived by the user to the real physical space has not been fully developed. Therefore, augmented reality based navigation systems for assisting medical procedure are not yet realized.

Furthermore, many of the waveguide based augmented reality/virtual reality displays in current arts that are able to display virtual images with various depths suffer focal rivalry problem. This is due to the fact that the distance of the display screen (from the eyes of the user) on which the eyes of the user focus on does not match the depth perception of the virtual image perceived by the viewer. This may cause discomfort and unable to focus on the real object and virtual image at the same time for the user.

Based on the above reasons, a novel augmented reality system for real space navigation that can resolve the above problems is desired.

SUMMARY

The present invention is advantageous relative to the prior arts in terms of overcoming focal rivalry and vergence accommodation conflict (VAC) in virtual/mix reality displays. In the field of augmented reality or mix reality, the depth perception and 3-dimensional effect of a virtual image is often rendered via parallax images technology. The parallax images of a virtual object for the left and right eye are displayed respectively on a screen that is at a fix distance from the viewer's eyes; however, this distance is often time different from the depth perception of the apparent point of the virtual image rendered. Furthermore, when the virtual image is intended to be superimposed on a real object to create augmented or mix reality, since the depth of the real object and the screen are at different distance from the viewer's eyes, the virtual image displaced by the screen and the real object cannot be focused by the eyes of the viewer simultaneously.

The present invention eliminates the usage of display screen and implement direct retinal scanning technology to project image onto the retina of the viewer's eyes. As a result, the viewer no longer needs to fixate on a fixed screen. In addition, the virtual image is projected into the eyes of the viewer with a convergence angle that is in consistence with binocular natural vision. In other words, the depth perception of a virtual image matches the convergence angle under natural vision. Thereby, both focal rivalry and VAC are eliminated in the present invention.

The augmented reality assisted system for performing a medical procedure on a patient comprises: a navigation module, for determining a set of spatial coordinates corresponding a position in a three dimensional real space for each of a plurality of navigation landmarks based on a diagnostic information of a patient, the plurality of navigation landmarks corresponding to target locations or target orientations of a surgical instrument in the three dimensional real space for performing the medical procedure; and a virtual image display module for displaying a virtual image correlated to one of the plurality of navigation landmarks such that the virtual image is perceived by a user to be at the position in the three dimensional real space, the virtual image being composed of at least one binocular pixels, each of the binocular pixels is formed by a first light signal projecting to a first retina of the user and a second light signal projecting to a second retina of the user. The virtual image display module comprises a left light signal projector and a right light signal projector. The left light signal projector and a right light signal projector may use laser as its light source. In one embodiment, the left light signal projector and a right light signal projector are laser beam scanning projector (LBS projector) which may comprise a red color light laser, a green color light laser, and a blue color light laser, a light color modifier, such as Dichroic combiner and Polarizing combiner, and a two dimensional (2D) adjustable reflector, such as a 2D electromechanical system ("MEMS") mirror. The 2D adjustable reflector can be replaced by two one dimensional (1D) reflectors, such as two 1D MEMS mirror. As an example, the LBS projector sequentially generates and scans light signals one by one to form a 2D image at a predetermined resolution, for example 1280×720 pixels per frame. Thus, one light signal for one pixel is generated and projected at a time towards the combiners.

The depth coordinate perceived by the user in the real space of each of the at least one binocular pixels having a specific horizontal coordinate and vertical coordinate is rendered by projecting the first light signal and the second light signal to a pair of designated locations respectively on surface of the first retina and the second retina that is specific for perception of the depth coordinate regardless a projection angle of the first light signal onto the first retina and a projection angle of the second light signal onto the second retina.

According to an embodiment of the present invention, the virtual image display module is a head wearable device, the set of spatial coordinates, the depth coordinate, the horizontal coordinate, and the vertical coordinate are measured with respect to the location of the head wearable device. In other embodiment of the present invention, the set of spatial coordinates, the depth coordinate, the horizontal coordinate, and the vertical coordinate are measured relative to the navigation module. The vertical coordinate or the horizontal coordinate perceived by the user in the real space of the at least one binocular pixel of the virtual image are rendered by projecting the first light signal and the second light signal to a pair of designated locations on surface of the first retina and the second retina having vertical positions or horizontal position corresponding to the vertical coordinate or the horizontal coordinate regardless the projection angle of the first light signal onto the first retina and the projection angle of the second light signal onto the second retina.

According to an embodiment of the present invention, the pair of designated locations comprises a first designated location and a second designated location. A variation in the depth coordinate of each of the at least one binocular pixels perceived by the user is rendered by changing a relative distance between the first designated location and the second designated location.

According to an embodiment of the present invention, the surgical instrument comprises an insertion portion for inserting into the patient, the medical imaging device is coaxially provided in proximity to the insertion portion. The surgical instrument may further comprise an orientation detection module for determining an orientation of the surgical instrument relative to the real space. The surgical instrument may also further comprise a penetration depth detection module for determining a depth of penetration of the surgical instrument into the patient.

According to an embodiment of the present invention, the medical imaging device may provide the diagnostic information related to a spatial location of each of a plurality of physiological or anatomical features of the patient. The medical imaging device may provide real-time information related to the patient. The medical imaging device may further provide real-time information related to a spatial deviation of one of the plurality of alignment reference points relative to one of the plurality of navigation landmarks.

According to an embodiment of the present invention, a plurality of alignment reference points are assigned to the surgical instrument, a position of each of the plurality of alignment references points are determined by navigation module. The navigation module respectively determines a spatial deviation of one of the plurality of alignment reference points relative to one of the plurality of navigation landmarks. The virtual image module may output a visual cue to the user when the spatial deviation is larger than a first predetermined value or smaller than a second predetermined value.

DETAILED DESCRIPTION OF PREFERRED EMBODIMENTS

The terminology used in the description presented below is intended to be interpreted in its broadest reasonable manner, even though it is used in conjunction with a detailed description of certain specific embodiments of the technology. Certain terms may even be emphasized below; however, any terminology intended to be interpreted in any restricted manner will be specifically defined as such in this Detailed Description section.

Figure 1:
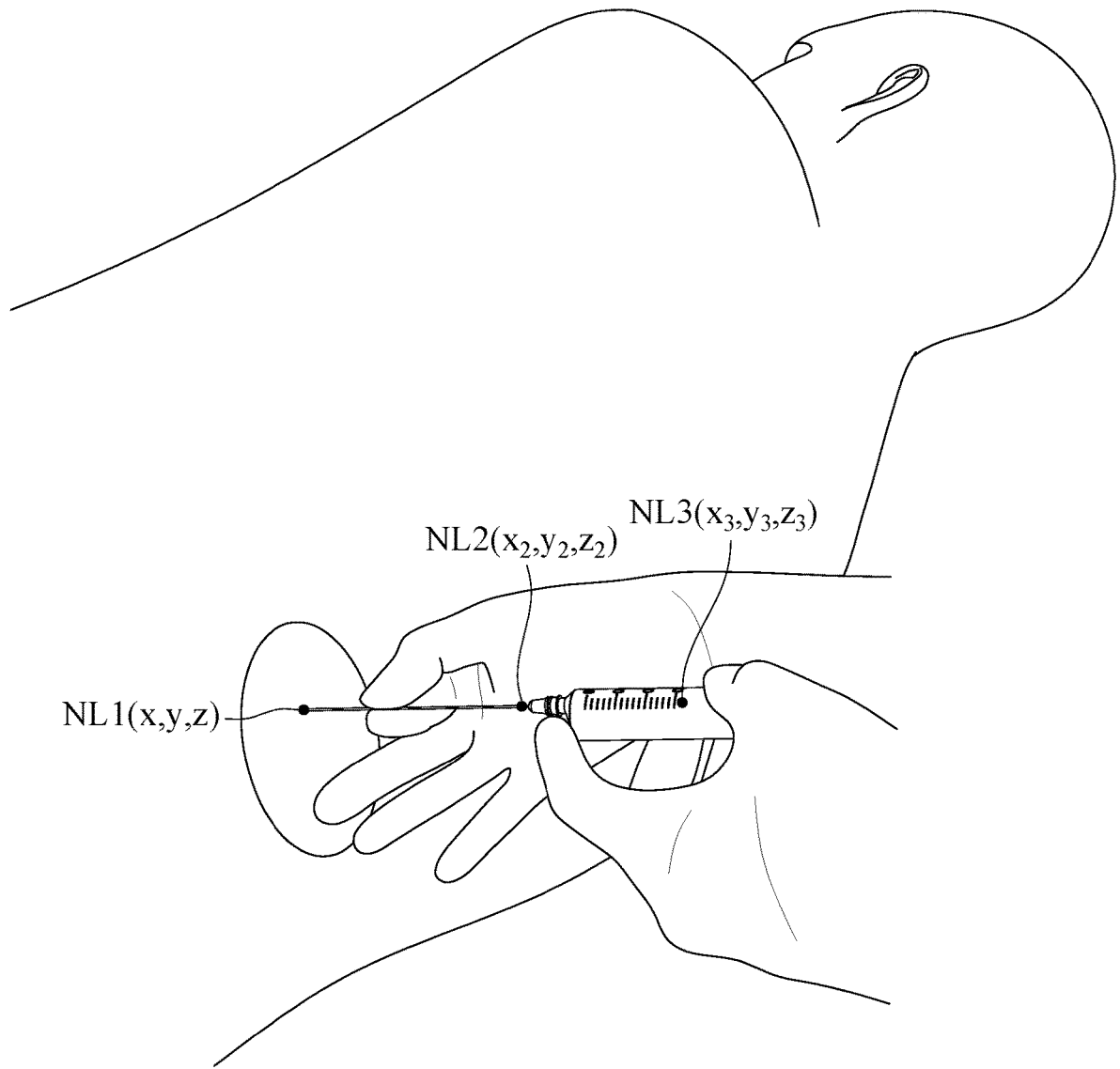
FIG. 1 illustrates the navigation landmarks in accordance with the embodiment of the present invention.

In the present invention, navigation landmarks are utilized to guide a user to complete a task which requires precise maneuver of equipment, tools, or human hands . . . etc. in three dimensional space; example of which may be medical procedures, or dental procedures. In some instances, the navigation landmarks are sets of spatial coordinates which indicate the correct locations or orientations of an equipment operated by a human to complete the task; for example (with reference to FIG. 1), the navigation landmarks may comprise coordinates indicating the location on the patient for the anesthetist to perform injection of epidural anesthesia. The navigation landmarks may also comprise a plurality of coordinates to indicate the correct location of the tip of the epidural needle, as well as the tail portion of the syringe so as to illustrate the correct orientation/angle of injection. With reference to FIG. 1, the navigation landmarks are denoted as NL1, NL2 . . . etc. The coordinates of the navigation landmarks in this example may be predetermined based on the medical imaging data of the patient, which may, for example, show the locations of the gaps between the vertebrae bones of the patient. The coordinates of the navigation landmarks indicate the proper orientation and location for epidural needle insertion to successfully insert the epidural needle in between the gap of the vertebrae bones of the patient while avoiding damage to the nerve system. In some other examples the navigation landmarks may indicate multiple position coordinates for a dentist to perform dental implant. In the present invention, augmented reality based display may display virtual images corresponding to the locations of the navigation landmarks, so the user can view the correct locations and orientations in three dimensional real space for performing the tasks. A person having ordinary skill in the art may understand that the present invention can be applied to other usage without deviating from the spirit of the present invention.

Figure 2:
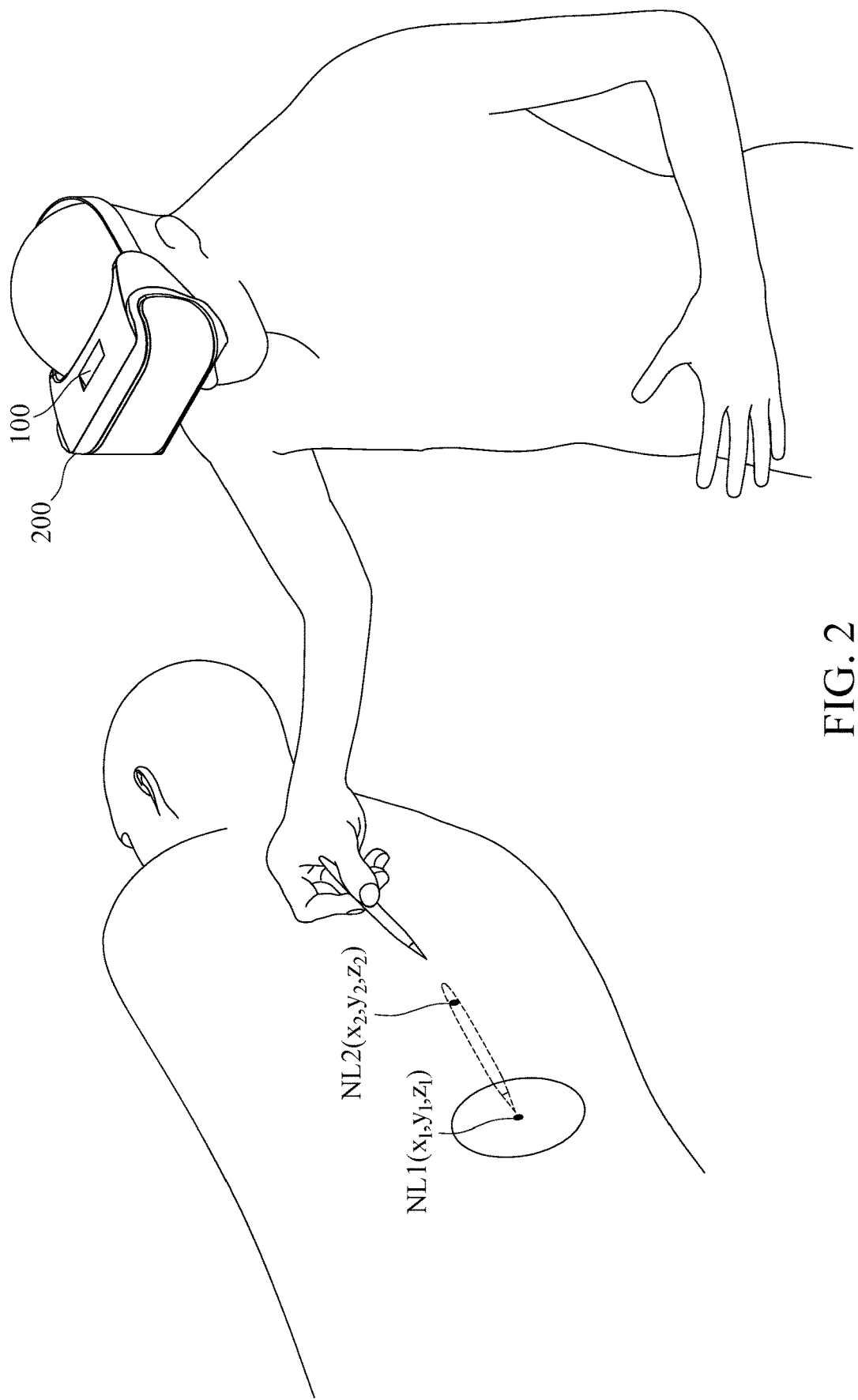
FIG. 2 illustrates the virtual image of the navigation landmarks and the augmented reality system for real space navigation in accordance with the embodiment of the present invention.

The following describes the augmented reality system for real space navigation which can be applied to varieties of circumstances. With reference to FIG. 2, the augmented reality system for real space navigation comprises a navigation module 100 and a virtual image display module 200. The navigation module 100 determines a set of spatial coordinates corresponding a position in a three dimensional real space for each of a plurality of navigation landmarks. More specifically, the navigation module 100 may receive data related to criteria which decide the locations of the navigation landmarks for a specific task. The navigation module 100 translates said data into three dimensional coordinates in real space with respect to a reference point. The reference point is designated as the origin (e.g., having a coordinate of (0, 0, 0)) of the coordinate system. As an example, the navigation module 100 may set the reference point at a point of the virtual image display module 200, a designated location in the real space, or at a point of the navigation module 100 . . . etc., depending on the embodiment. The plurality of navigation landmarks corresponds to target locations or target orientations of a task subject in the three dimensional real space for performing the task. For example, in the case which the task is performing intravenous anesthetics injection, the task subject may be the injection epidural needle. For other types of medical procedures, the task subjects may be the corresponding tools for performing the medical procedures. In some embodiments, the navigation module 100 is provided on the virtual image display module 200, or the navigation module 100 is an indoor positioning system provided separately to the virtual image display module 200.

For exemplary purpose, the navigation module 100 in accordance with the present invention may comprise a positioning unit for determining the location of the user (when the origin is not set at the head wearable device of the user), the position of the surgical instrument and the position of the site of the operation . . . etc. The positioning unit may be implemented with GPS (indoor or outdoor), mobile phone network, or WI-FI for outdoor positioning method. The positioning unit may be implemented with UWB, Bluetooth, wireless network or beacon for indoor positioning. In the embodiment which the navigation module 100 is provided on the heard wearable device, the navigation module 100 may also comprise a depth sensing unit. The depth sensing unit may be used to measure the distance between any points on a target object and the user (more specifically, midpoint between two eyes of the user). The position of the user's hand or a surgical instrument may also be measured by the depth sensing unit. A depth map may be used for tracking the movement of the target objects, the surgical instrument and/or hands. The depth map is created by the depth sensing unit and/or a camera. The depth map is further used to cluster the target objects and the hands. The depth sensing unit may be implemented in the form of a depth sensing camera. The depth sensing camera captures a 2-denstional image or a 3-dimensional real-time image of a target object and the distance between the camera and the target object can also be determined by the depth sensing unit. The navigation module 100 may further comprise an inertial measurement unit (IMU) for assisting the determination the position and orientation of the user.

In some embodiments of the present invention, the virtual image display module 200 may comprise an eye-tracking unit for determining the selection of a target object of the user by the visual axes of the user. The visual axes of the user are determined by eye-tracking unit. Eye-tracking is realized by eye-tracking cameras, or the electrical signal measurements of the eye movements. The virtual image display module 200 may also comprise a hand gesture recognition unit. The hand gestures and the location of the of the hands may be captured by the depth sensing unit or camera. The depth sensing unit or camera provides information regarding the hand gesture to the hand gesture recognition unit, and the hand gesture is then recognized by the hand gesture recognition unit. The virtual image display module 200 may further comprise an object recognition unit. Images and locations of the target objects are captured by the depth sensing unit or the depth sensing camera. The object recognition unit performs object recognition on the target objects based on the images of the target objects. In some instances, the object recognition unit may recognize the surgical instrument, the hands of the user, and the patient.

The virtual image display module 200 is configured to display a virtual image correlated to any one of the plurality of navigation landmarks for the user to visualize the navigation landmarks for navigation purpose. Particularly, the virtual image is perceived by a user to be at the position in the three dimensional real space. As an example, in the case which the user of the present invention is performing a medical procedure, the virtual image may be a circular spot indicating the location for the insertion of the surgical instrument on the patient; or the virtual image may resemble a virtual image of the surgical instrument which indicate the desired location or orientation of the real surgical instrument, as shown in FIG. 2. Although the navigation landmark may be expressed as a coordinate of a point in the three dimensional real space, the visual representation of the navigation landmark may be centered at the coordinate of the navigation landmark and occupies a small area in the three dimensional space; or, the virtual image may be rendered based on the locations of the navigation landmarks. Therefore, the virtual image may be composed of at least one binocular pixels (as shown in FIG. 2). For a retinal scanning based augmented display system, each of the binocular pixels is formed by a first light signal projecting to a first retina of the user and a second light signal projecting to a second retina of the user. The present invention utilizes retina scanning technology for rending virtual images of navigation landmarks. The method for rending virtual images and binocular pixels to be perceived by the user at a specific real spatial location will be described in detail below.

Figure 3A:
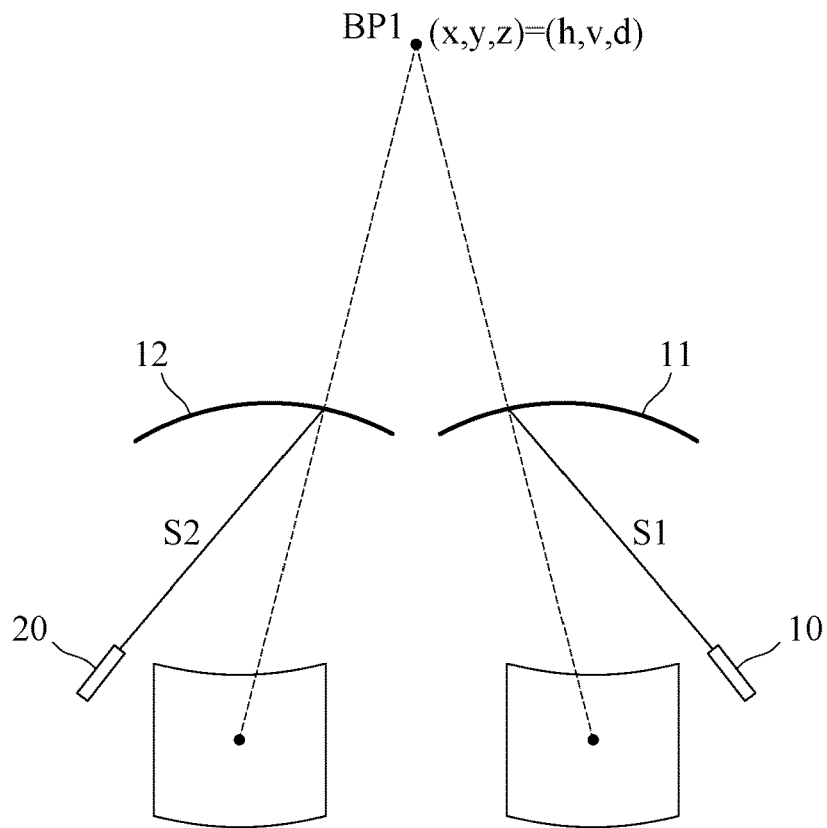
FIG. 3A illustrates the navigation landmarks and the augmented reality system for real space navigation in accordance with the embodiment of the present invention.

With reference to FIG. 3A, in the present invention, the virtual image display module 200 comprises a first light signal generator 10 (e.g., right light signal generator), a first combiner (e.g., right combiner), a second light signal generator 20 (e.g., left light signal generator), and a second combiner (e.g., left combiner). The first light signal generator generates a first light signal; the first combiner 11 redirects the first light signal towards the first retina of a user to display a first pixel p1. By the same token, the second light signal generator 20 generates a second light signal; the second combiner 21 redirects the second light signal towards the second retina of the user to display a second pixel p2.

The virtual image display module comprises. The first and second light signal projectors 10, 20 may use laser as its light source. In one embodiment, the first and second light signal projectors 10, 20 are laser beam scanning projector (LBS projector) which may comprise a red color light laser, a green color light laser, and a blue color light laser, a light color modifier, such as Dichroic combiner and Polarizing combiner, and a two dimensional (2D) adjustable reflector, such as a 2D electromechanical system ("MEMS") mirror. The 2D adjustable reflector can be replaced by two one dimensional (1D) reflector, such as two 1 D MEMS mirror. As an example, the LBS projector sequentially generates and scans light signals one by one to form a 2D image at a predetermined resolution, for example 1280×720 pixels per frame. Thus, one light signal for one pixel is generated and projected at a time towards the combiners. For a viewer to see such a 2D image from one eye, the LBS projector has to sequentially generate light signals for each pixel, for example 1280×720 light signals, within the time period of persistence of vision, for example ⅛ second. Thus, the time duration of each light signal is about 60.28 nanosecond.

Figure 3B:
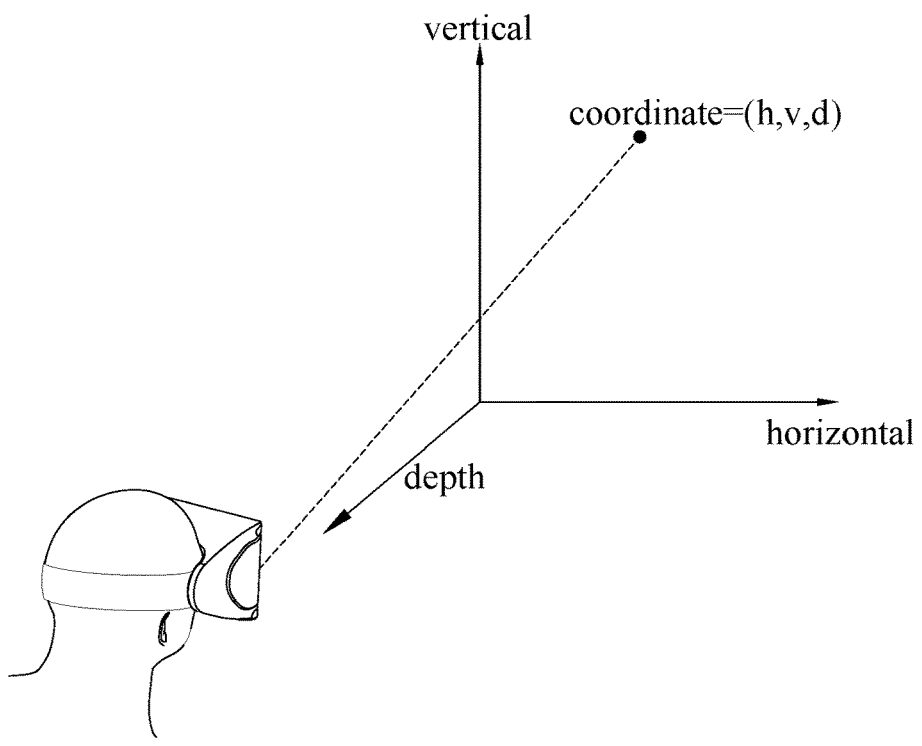
FIG. 3B illustrates an exemplary coordinate system in accordance with the embodiment of the present invention.

After the first eye and the second eye of the user perceive the first light signal and the second light signal, the human brain creates an image of a binocular pixel (e.g., BP1) through fusion of the image of the first light pixel and the second light pixel. The binocular pixel is perceived by the user to have a specific 3-dimensional coordinates. For the convenience of describing the current invention, the origin of the coordinate system may be set at the center of the virtual image display module 200 (which may be a head wearable device); the 3-dimensional coordinates correspond to a specific horizontal coordinate, vertical coordinate, and a depth coordinate relative to the head wearable device (as shown in FIG. 3B).

Figure 4:
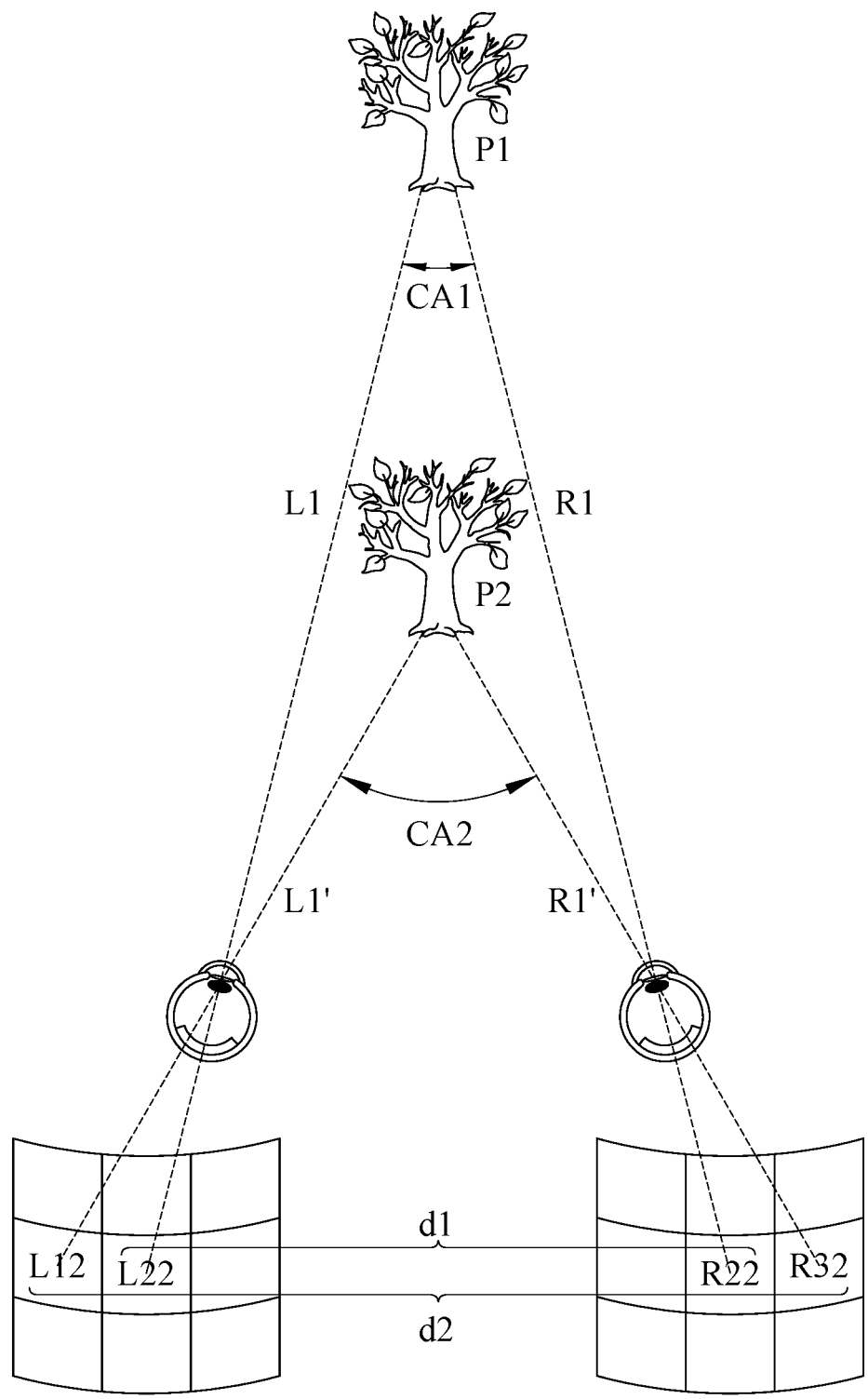
FIG. 4 illustrates the principal of natural binocular vision in accordance with present invention.

It is readily known that the horizontal and vertical position of a binocular pixel in 3-dimensional space perceived by the user is directly related to the horizontal and vertical position on the first retina and the second retina where the first light signal and the second light signal are respectively projected and received. However, the present invention addresses that the depth position of the binocular pixel perceived by the user is also correlated to the horizontal and vertical position on the first retina and the second retina where the first light signal and the second light signal are respectively projected and received. With reference to FIG. 4, which illustrates a perception of the horizontal, vertical and depth position of an object in 3D space according to natural binocular vision of humans. For the convenience of illustrating the principle of human vision and retina scanning, the retina of the first eye and the second eye of the user are drawn as matrixes, each of the matrix elements correspond to a specific horizontal and vertical location on the retina. According to natural vision, the first right light instance R1 from the object arrives at matrix element R22 of the first retina. The corresponding second light instance L1 from the object arrives at matrix element L22 of the second retina. In addition to parallax information of the object contained in R1 and L1, the depth perception of the user is also dependent upon the convergence angle CA1 between the first light instance R1 and the second light instance L1. As the depth of the object perceived by the viewer increases, the convergence angle decreases; conversely, as the depth of the object perceived by the viewer decreases, the convergence angle increases. Specifically, as shown in FIG. 4, suppose the object is moved from a position p1 to p2, the convergence angle changes from CA1 to CA2 (with CA2>CA1); meanwhile, the location on the first retina receiving the first light instance changes from R22 to R23, and the location on the second retina receiving the second light instance changes from L22 to L12. Evidently, the depth perception of a object is at least in part related to the convergence angle between the first light instance and the second light instance entering the eyes of the viewer (in additional to parallax images). In natural vision, although there may be infinite number of first light instance and second light instance from a point of the object due to light scattering; however, all of the first instances and the second instances are respectively converged to a single location due to the effect of the lens of the eyes; therefore, only one instance is shown in FIG. 4. Furthermore, according to FIG. 4, it can be seen that each convergence angle formed between the first light instance R1 and the second light instance L1 has a corresponding relative horizontal distance between the first light instance R1 and the second light instance L1 on the two retinae (shown as d1 and d2). Thus, it can also be regarded that the depth of object perceived by the user is correlated to the relative horizontal distance between the location where the first light instance R1 is projected on the first retina and the corresponding location where the second light instance L1 is projected on the second retina. In other words, the deeper an object is perceived by the user, the smaller the relative horizontal distance between the location on the retina for receiving the first light signal and the location on the retina for receiving the second light signal. However, from another aspect, the relative distance between the first light instance and the second light instance can be measured at locations close to the front area of the pupils. In this regard, the relative horizontal distance between two light instances forming a larger convergence angle (the object is closer to the viewer) will be smaller than the relative horizontal distance between two light instances forming a smaller convergence angle (the object is farther from the viewer). In other words, the deeper a real object is perceived by the user, the larger the relative horizontal distance between the light instance forming the image of the real object before entering the pupil. Based upon the principle above, the depth perception of an object can be manipulated by varying the relative distance between the light instances forming the image prior to entering the eye, or by varying the relative distance between the locations on the retinae which receive the light instances.

Figure 5:
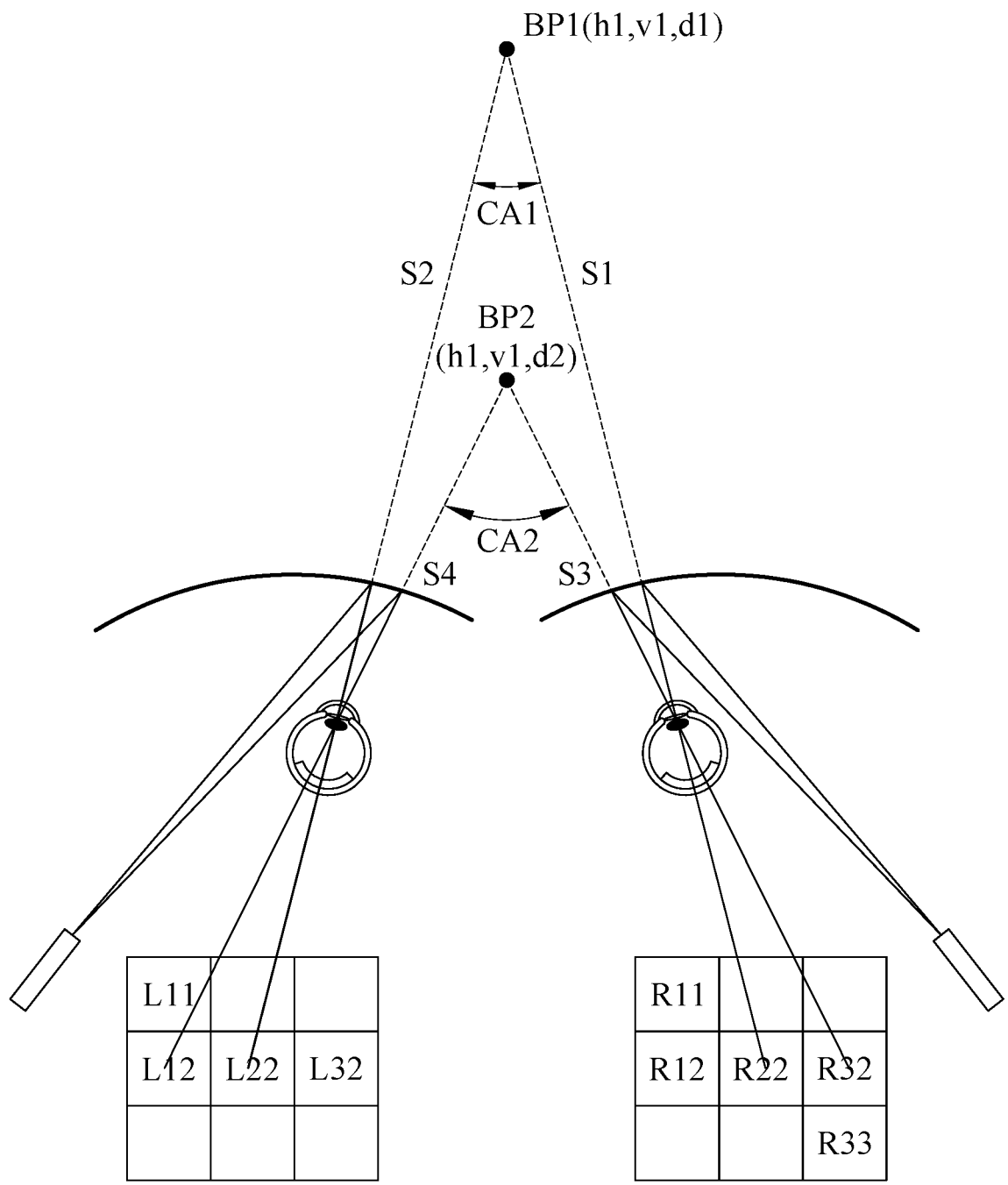
FIG. 5 illustrates the principal of rendering various depth perception at specific horizontal and vertical coordinate coordinates in accordance with the embodiment of the present invention.

With reference to FIG. 5, which illustrates the method for rendering depth perception based upon the principle mentioned above in accordance with the present invention. FIG. 5 shows a first binocular pixel BP1 formed by fusion of the first light signal S1 and the second light signal S2 having a first convergence angle CA1; and a second binocular pixel BP2 formed by fusion of the third light signal S3 and the fourth light signal S4 having a second convergence angle CA2. The first binocular pixel BP1 is rendered by projecting light signals to the pair of designated locations R22 (first designated location) and L22 (second designated location). The first binocular pixel BP1 is perceived by the user to have a larger depth (i.e., further away from the user) than the second binocular pixel BP2. The second binocular pixel BP2 is rendered by projecting light signals to the pair of designated locations R32 (first designated location) and L12 (second designated location). The horizontal distance between the third light signal S3 and the fourth light signal S4 on the retina (distance between R32 and L12) is larger than the horizontal distance between the first light signal S1 and the second light signal S2 on the retina (R22 and L22). As shown in FIG. 5, it can be understood that in order to render a binocular pixel having a depth coordinate of d1 at horizontal coordinate h1 and vertical coordinate of v1, light signals need to be provided to the pair designated location of R22 and L22. If a binocular pixel having a depth coordinate of d2 with the same horizontal coordinate h1 and vertical coordinate of v1 needs to be rendered, light signal needs to be provided to the pair designated location of R32 and L12. Therefore, variation in the depth coordinate of each of the at least one binocular pixel perceived by the user can be rendered by projecting light signals to different first designated locations and the second designated locations.

Based upon the principle described above, in an embodiment which the origin of the three dimensional coordinate system is set at the center of the head wearable device, the depth coordinate perceived by the user in the real space of each of the binocular pixels having a specific horizontal coordinate and vertical coordinate is rendered by projecting the first light signal and the second light signal to a pair of designated locations (e.g., R22 and L22, or R32 and L12) respectively on surface of the first retina and the second retina. Each pair of designated locations renders a specific depth coordinate perception for the user. Although in the description above, a matrix of 3×3 is used to illustrate this principle of human binocular vision, it is apparent that retina can be divided into more than a 3×3 matrix (e.g., 100×100 matrix or 1000×1000 matrix). Furthermore, the example is used to demonstrate the idea that for every depth coordinate, there exists a designated location on the first retina and another corresponding designated location on the second retina (pair of designated locations) on which the light signal can be projected so that the user can perceive a binocular pixel at that specific depth coordinate. In addition, the vertical coordinate or the horizontal coordinate perceived by the user in the real space of the at least one binocular pixel of the virtual image are rendered by projecting the first light signal and the second light signal to a pair of designated locations on surface of the first retina and the second retina having vertical positions or horizontal position corresponding to the vertical coordinate or the horizontal coordinate regardless the projection angle of the first light signal onto the first retina and the projection angle of the second light signal onto the second retina. As long as the light signals are projected to the specific locations on the retinae, the eyes of the human are able to perceive a binocular pixel at the corresponding locations in real space regardless the angle of the incident lights on the retina.

Figure 6:
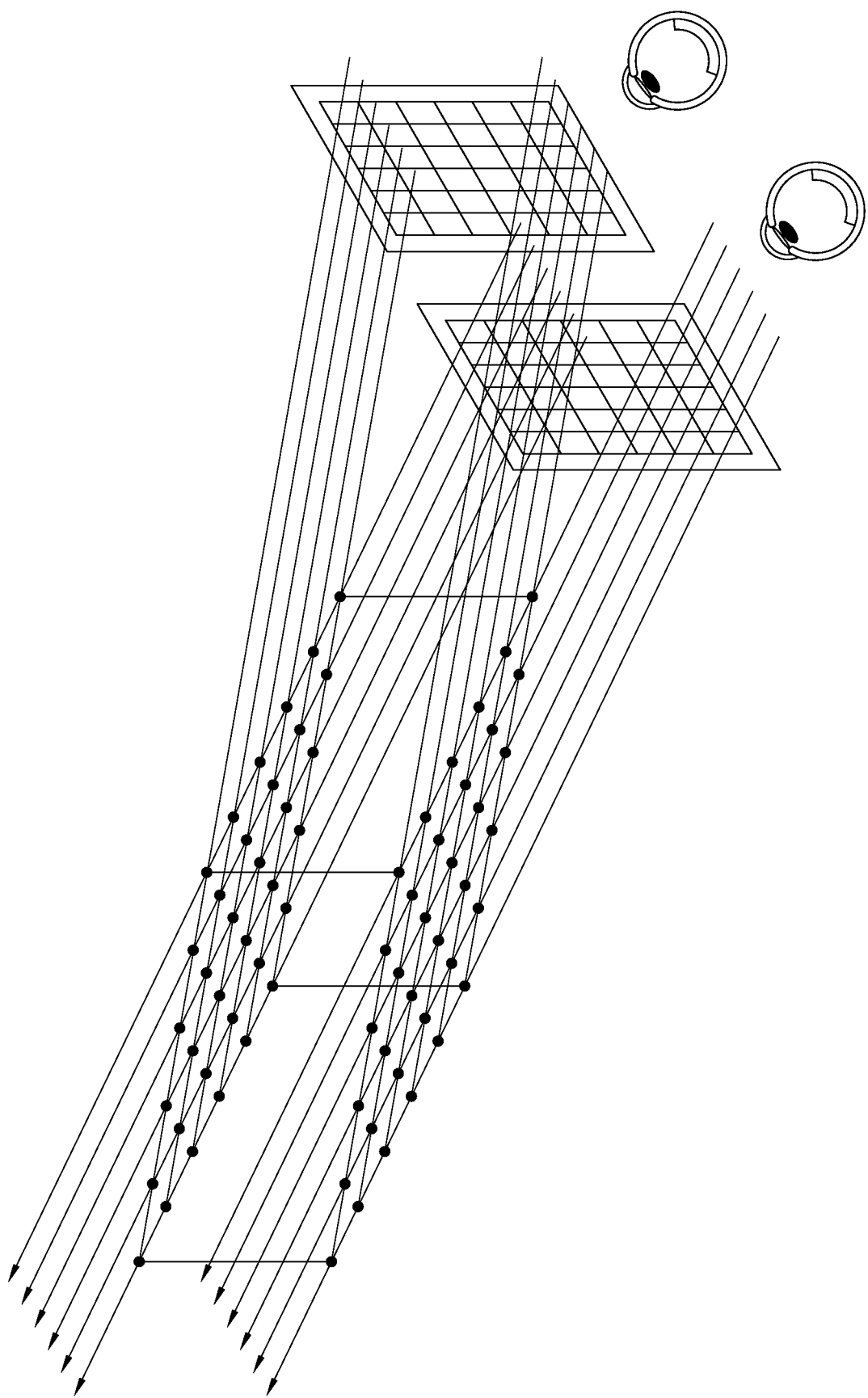
FIG. 6 illustrates the principal of rendering multiple binocular pixel in 3-dimensional real space in accordance with the embodiment of the present invention.

FIG. 6 further illustrates the relationship between the binocular pixels and the pairs of designated locations which forms the binocular pixels. In this example, the first and second retina are respectively divided into 36 (6×6) designated locations. It is known that in order for fusion of vision to happen, the image projected to the right eye and the corresponding image projected to the left eye need to have similar vertical position (relative to the eyes of the human). Therefore, the pair of designated locations need to have substantially the same vertical position (relative to the eyes of the human). In FIG. 6, the light path extension of one light signal intersects the light path extension of the corresponding light signal on the same row (i.e., same vertical position). Based on this prerequisite, and after taking the vertical coordinate and horizontal coordinate into consideration, a total of 216 (6×6×6) virtual binocular pixels with different 3-dimensional coordinates (shown as a dot) can be created.

Figures 7A, 7B:
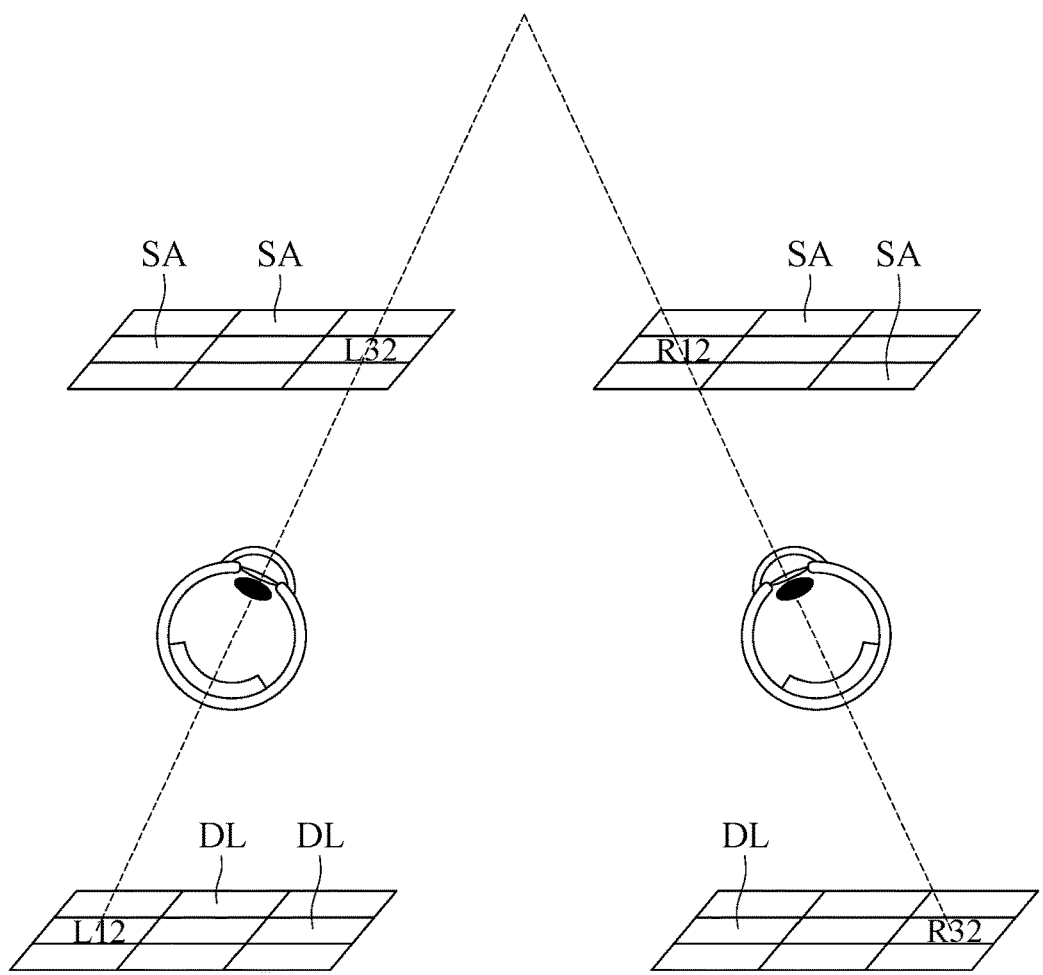
FIG. 7A demonstrates a lookup table containing pairs of designated locations with their corresponding spatial coordinates.
FIG. 7B demonstrates the method for accurately projecting light signals to the desired designated locations.

With reference to FIG. 7A, a look-up table may be constructed for the virtual image display module 200 to quickly identify the correct pair of designated location for rendering a depth coordinate at specific vertical and horizontal coordinate for a binocular pixel. For example, 216 virtual binocular pixels, numbering from 1 to 216, are formed by projecting light signals to 36 (6×6) designated location on the first retina and 36 (6×6) designated location on the second retina. The first (1st) binocular pixel BP(1) having horizontal coordinate h1, vertical coordinate v1, and depth coordinate d1 is rendered by the pair of designated locations R(11) and L(11); the second (2nd) binocular pixel BP(2) having horizontal coordinate h2, vertical coordinate v2, and depth coordinate d2 is rendered by the pair of designated locations R(12) and left pixel L(11). Thus, in order to display a binocular pixel at a specific 3-dimensional coordinate in real space, the light signals projected into the left eye and the right eye of the user need to be received at the corresponding designated locations on the surface of the retinae of the user based on the information of the look up table.

In practice, in order to accurately project light signal to the desired designated locations on the retinae of the viewer, the locations where the projected light signal entering the pupils is a key factor to be considered. In other words, the location where the first and second light signal entering the pupils need to be controlled such that the light signals can incident on the correct location on the retinae so as to render a binocular pixel at a specific spatial location. The area right before the pupil receives the incoming light signal can also be viewed as a matrix and can be divided into several subunit areas, similar to that of the designated locations on the retina aforementioned (with reference to 7B). Each of the subunit areas SA correlate to a designated location DL on the retain. Therefore, when a light signal enters the pupil via specific subunit areas with specific angles, the corresponding designated locations on the retain which receive the light signal can be anticipated. In an embodiment, a lookup table may also be constructed to determine the location of entering the pupil for the light signal to ensure the light signal can be received by the desired designated location on the retina. In one embodiment, the relationship between the subunit areas and the corresponding designated area of the retina area shown in FIG. 7B. In this example, for the light signals to be received by the pair of designated locations R32 and L12 on the retinae, the light signals need to go through subunit R12 and L32 in front of the area before entering the pupil. Therefore, in order to change the depth of a binocular pixel perceived by the viewer from one position to another, the light signals can be projected via different pair of subunit areas SA that correlate to the target designated locations on the retina, thereby, allowing the target pair of designated locations to receive the light signals.

Figure 8:
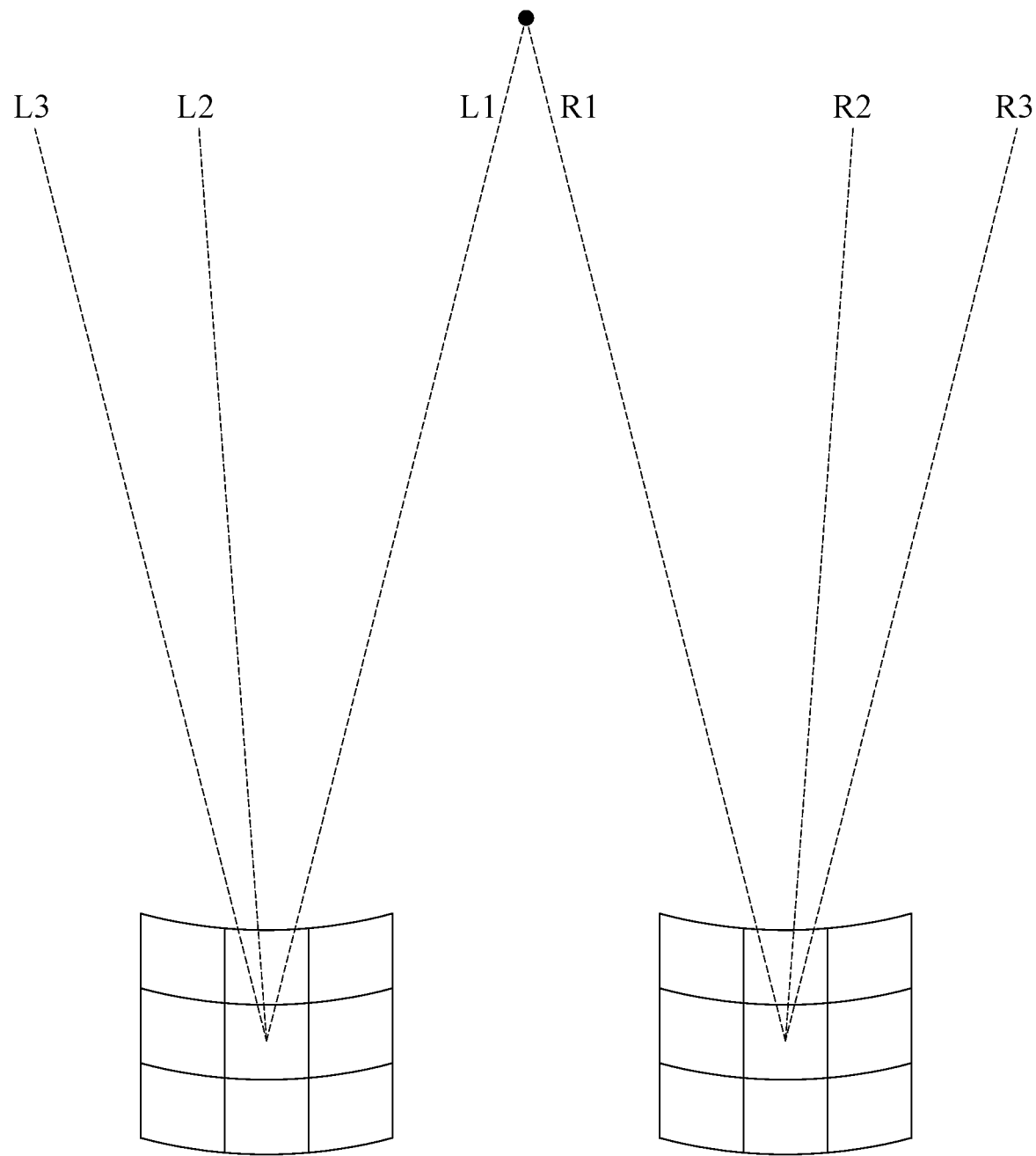
FIG. 8 illustrates the principal of rendering multiple binocular pixel in 3-dimensional real space in accordance with another embodiment of the present invention.

Furthermore, with reference to FIG. 8, based on the above principle for rendering depth coordinate of a binocular pixel, the depth perception of the binocular pixel is independent of the projection angle of the first and second light signal into the first and second eye of the user. As long as the pair of designated locations corresponding to a particular depth coordinate receives light signals, a binocular pixel having said depth coordinate can be rendered regardless the projection angle of the first light signal onto the first retina and the projection angle of the second light signal onto the second retina. In the method of rendering depth perception mentioned above, each of the designated location has a fixed relative position on the retina. This means the designated locations cannot be randomly or artificially assigned; they are the result of human physiology and retina anatomy. When stimulated by light signals, each pair of designated locations can render a unique 3-dimensional coordinate for a binocular pixel and, and each pair of designated locations has a unique location on the retinae of the user. Furthermore, in order for the first light signal and the second light signal to be fused by the human brain to create a single binocular pixel, the information contained in the first light signal and the second light signal need to be substantially the same.

Figure 9A:
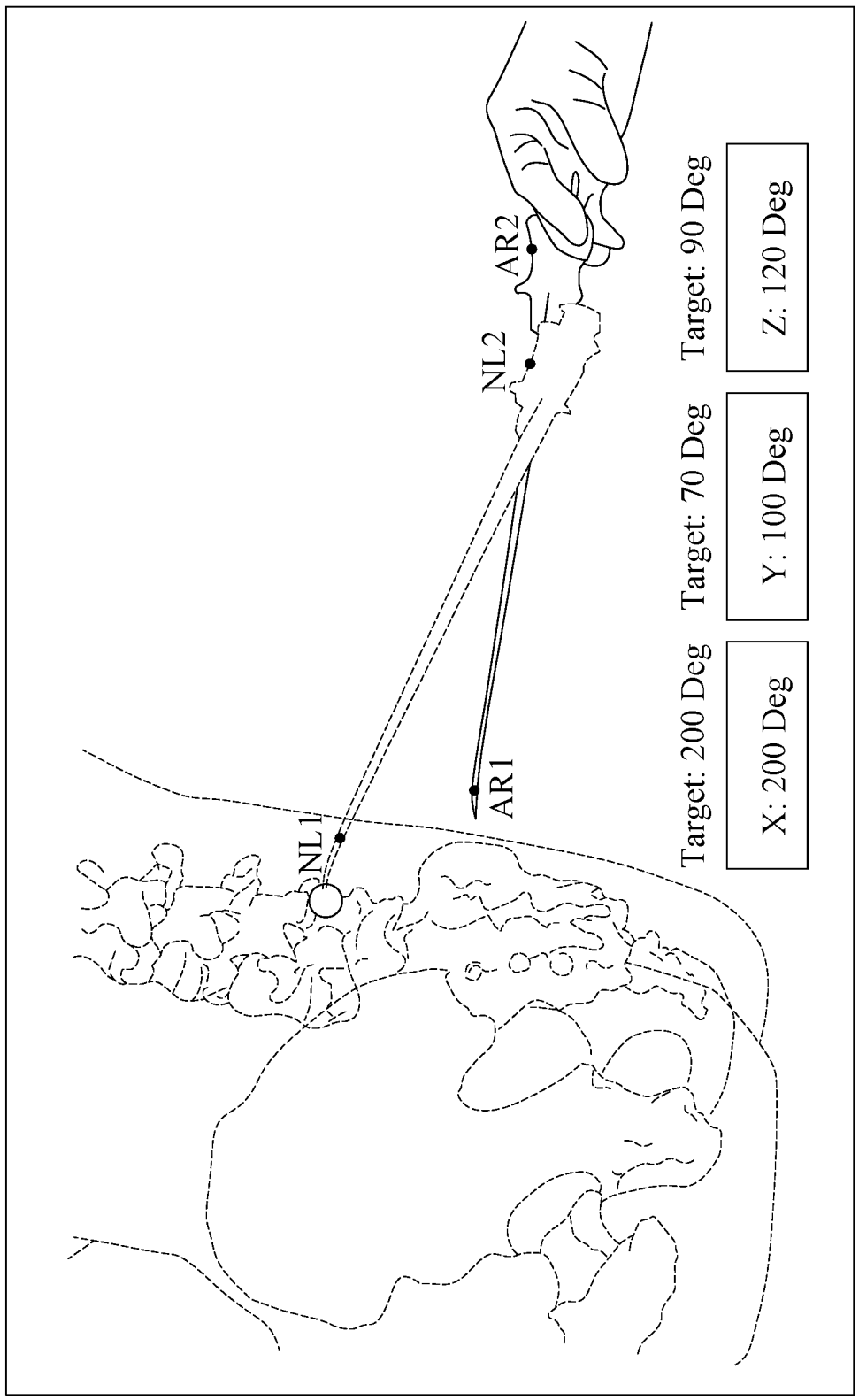
FIG. 9A illustrates an exemplary implementation of the present invention.
Figure 9B:
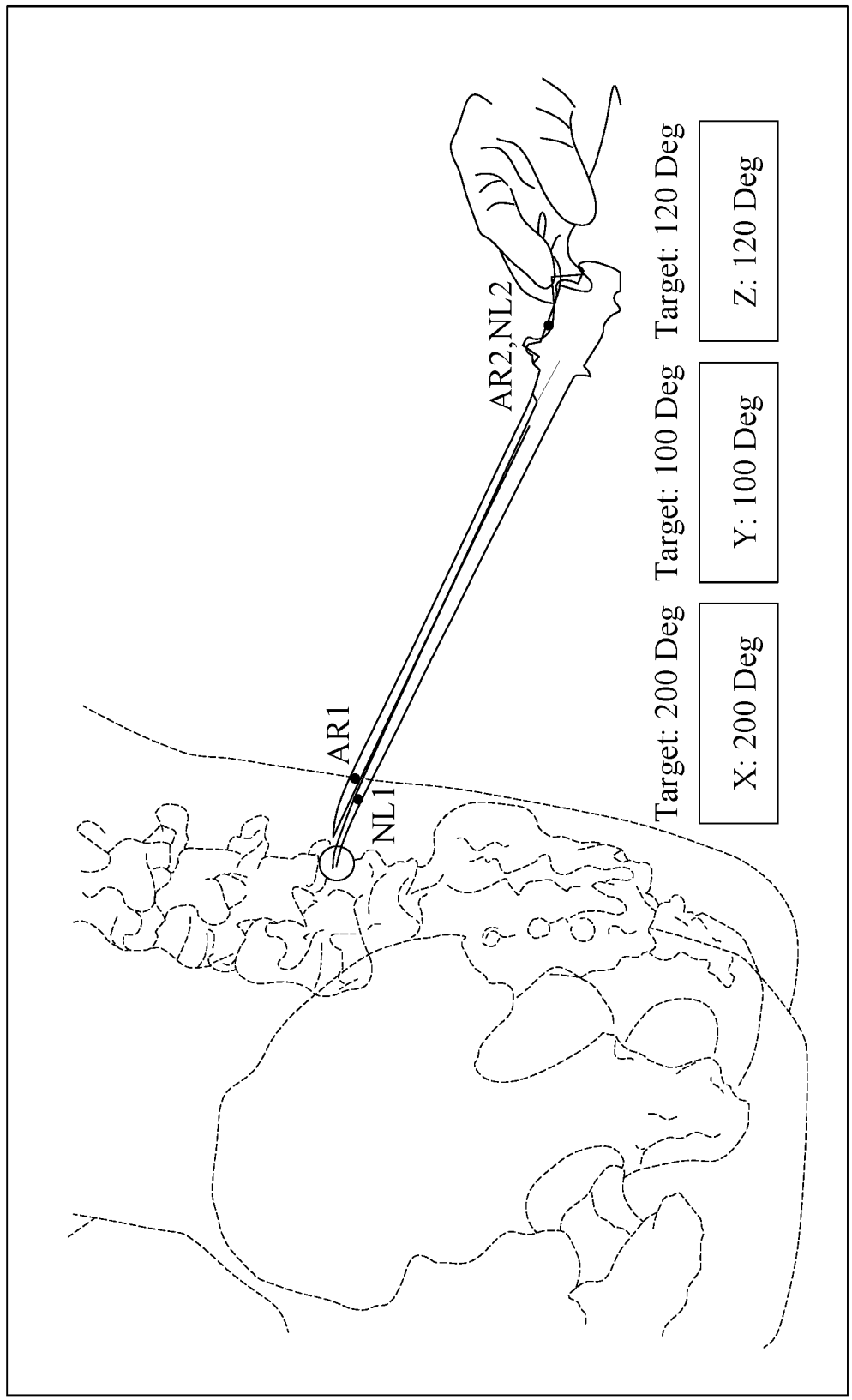
FIG. 9B illustrates an exemplary implementation of the present invention.

With the aforementioned method for rending a binocular pixel that can be perceived by the user to be at a specific location in 3-dimensional real space, the virtual image display module 200 is able to display an image at the specific location in 3-dimensional real space corresponding to the navigation landmark (as shown in FIGS. 9A and 9B). The image corresponding to the navigation landmark may be composed of at least one binocular pixel. In one example, the image of the navigation landmark may be displayed for the user, so the user knows exactly where (in the real three dimensional space) to perform the task (e.g., surgery or epidural needle insertion). The navigation landmark can also display the correct location and orientation of an equipment for performing the task (e.g., the orientation of the scalpel or epidural needle for performing surgery or epidural needle insertion).

Figure 10:
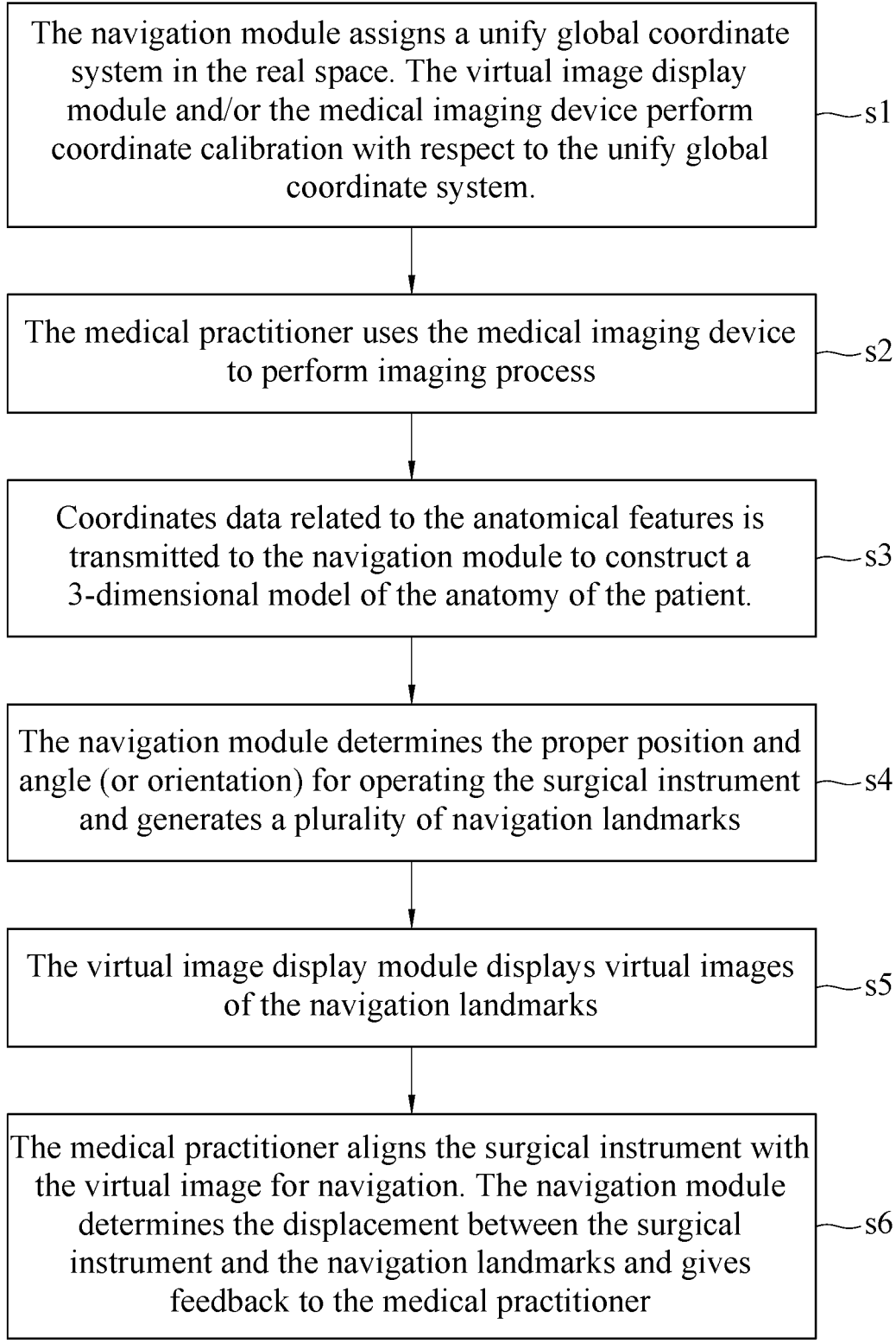
FIG. 10 illustrates and exemplary embodiment of a surgical procedure implementing the augmented reality system for real space navigation in accordance with the present invention.

With reference to FIG. 10, the following is an exemplary embodiment of a surgical procedure implementing the augmented reality system for real space navigation in accordance with the present invention. The surgical procedure may comprise the following steps:

(s1) The navigation module assigns a unify global coordinate system in the real space for the patient, the virtual image display module, the surgical instrument, and the medical practitioner. The virtual image display module and/or the medical imaging device perform coordinate calibration with respect to the unify global coordinate system (e.g., vertical coordinate, horizontal coordinate, and depth coordinate).

(s2) The medical practitioner uses the medical imaging device to perform imaging over a general area in proximity to a target surgical site on the patient. The medical imaging device may be a magnetic resonance imaging device, CT scan, or ultrasound imaging device. The imaging data is transformed into sets of spatial coordinate data related to the anatomical features in proximity to the target surgical site of the patient.

(s3) The sets of spatial coordinate data related to the anatomical features is transmitted to the navigation module to construct a 3-dimensional model of the anatomy of the patient.

(s4) The navigation module determines the proper position and angle (or orientation) for operating the surgical instrument in 3D real space based upon the 3-dimensional model of the anatomy of the patient. The navigation module generates a plurality of navigation landmarks correlated to the positions and angle (or orientation) of the surgical instrument for performing the surgical procedure.

(s5) The virtual image correlated to the navigation landmarks are displayed to the medical practitioner via the virtual image display module (e.g., head wearable device).

(s6) The medical practitioner can align the surgical instrument with the virtual image for navigation. The navigation module determines the deviation between the surgical instrument and the navigation landmarks and gives feedback to the medical practitioner.

The following description continues to use epidural anesthesia as an example for explaining the application of the augmented reality system for real space navigation in accordance with the present invention.

The augmented reality assisted system may comprise the navigation module 100 for determining a set of spatial coordinates corresponding a position in the three dimensional real space for each of a plurality of navigation landmarks. The navigation landmarks are defined based on a diagnostic information of a patient. For example, the diagnostic information may be a real-time ultrasonic scan image of the spine of the patient, which shows the locations of the vertebrae and the gaps between the vertebrae. A plurality of navigation landmarks may be defined by the navigation module 100, the navigation landmarks correspond to target locations or target orientations of a surgical instrument (e.g., epidural needle) in the three dimensional real space for performing the medical procedure (e.g., epidural anesthesia). For example, the navigation landmarks may show the best location and orientation for the epidural needle to be inserted into the space between vertebrae for epidural anesthesia.

The virtual image display module 200 displays a virtual image correlated to the plurality of navigation landmarks such that the virtual image is perceived by a user to be at the specific position in the three dimensional real space. The virtual image display in this embodiment may be a head wearable device. The origin of the coordinate system for expressing the coordinate of the navigation landmarks and the virtual images (depth coordinate, the horizontal coordinate, and the vertical coordinate) is set at the location of the head wearable device. The navigation module 100 may also be provided on the head wearable device in this embodiment.

The virtual image may be an arrow or an epidural needle for guiding the medical practitioner to hold the epidural needle with the correct orientation when inserting the epidural needle into the body of the patient. The virtual image is composed of at least one binocular pixel, each of the binocular pixels is formed by a first light signal projecting to a first retina of the user and a second light signal projecting to a second retina of the user, as mentioned earlier. In some embodiments, the location of the virtual image perceived by the user in the 3-dimensional space matches the correct location for inserting the epidural needle into the body of the patient. Additional two virtual images of two navigation landmarks illustrating the correct positions of two ends of the epidural needle may also be shown so the medical practitioner can match the position of the two ends of the actual epidural needle with the two virtual images of the navigation landmarks seen by the medical practitioner to obtain the correct orientation of the epidural needle.

In an alternative embodiment of the present invention, the virtual image may resemble the epidural needle for the medical practitioner to match the location and orientation of the actual epidural needle with the virtual image of the epidural needle. The relative distance between the medical practitioner and the virtual image perceived by the medical practitioner (who is wearing the head wearable device) may be dynamically adjusted based on the movement or change in position of the medical practitioner. The relative orientation of the virtual image perceived by the medical practitioner can also be adjusted dynamically in response to the change in location of the medical practitioner. This may be achieved by the position module dynamically calculating the 3-dimensional coordinate in real space relative to the origin (which may be set at the location of the head wearable device and moving along with the medical practitioner) of the navigation landmarks (or the virtual images); the virtual image display module 200 (i.e., the head wearable device) than dynamically adjusts and renders the virtual image based on the change in position of the medical practitioner. In this embodiment, the origin of the coordinate system may be set at the location of the virtual image display module 200 (i.e., the head wearable device). However, as mentioned earlier, the origin of the coordinate system may be set at locations other than the location of the virtual image display module 200, especially in the case which the navigation module 100 is not provided on the head wearable device. For example, in some instances, the origin may be set at the navigation module 100, and the position of the navigation module 100 may be fixed relative to a room where the surgery is performed. Nonetheless, the coordinates of the navigation landmarks and the head wearable device can be measured and calculated relative to the navigation module 100, and the position of the virtual image perceived by the medical practitioner can be adjusted based on the relative position between the origin of the coordinate system and the medical practitioner (who is wearing the head wearable device).

To enhance the alignment between the real epidural needle and the virtual image so the medical practitioner can perform epidural anesthesia with better accuracy, in some embodiments of the present invention, the navigation module 100 may assign a plurality of alignment reference points on the real epidural needle. In this embodiment, the navigation module 100 may further comprise an object recognition module for recognize the features of the real epidural needle and assign specific features as alignment reference points; and a position sensing module for sensing the location of these alignment reference points. The navigation landmarks may have a correlation with the alignment reference points. That is to say, in some instances, the navigation landmarks relate to the correct coordinates where the alignment reference points should be in the real space during epidural needle insertion. The navigation module 100 may be able to compare a location of the alignment reference point with a corresponding navigation landmark to determine a spatial deviation of the alignment reference point relative to their corresponding navigation landmark. Furthermore, the virtual image display module 200 may output a visual cue to alert the medical practitioner when the spatial deviation is larger than a pre-determined upper limit of allowable spatial deviation; or the virtual image display module 200 may output another visual cue to confirm that the epidural needle is on the correct path for insertion when the deviation is smaller than a pre-determined lower limit value.

Figure 11:
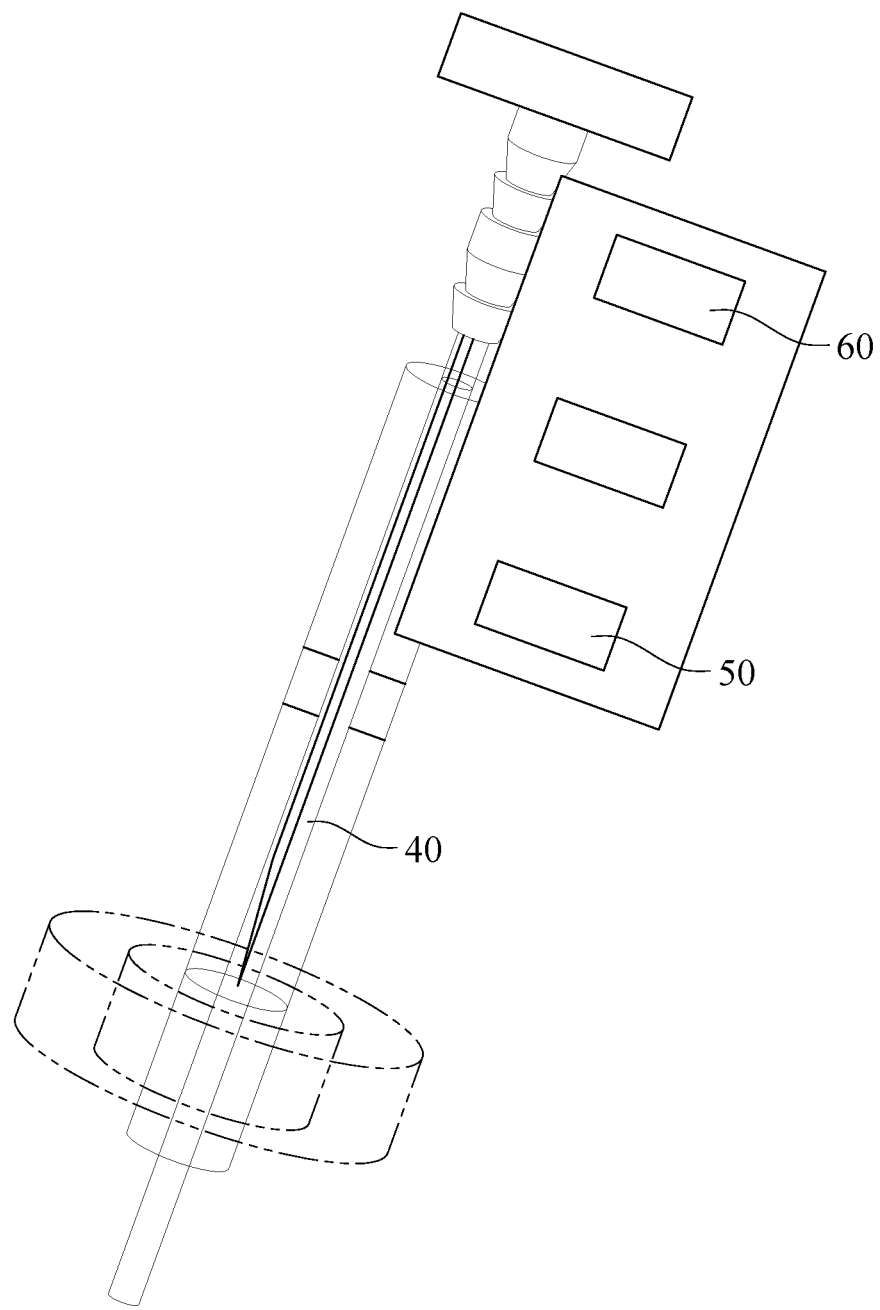
FIG. 11 illustrates and exemplary surgical instrument in accordance with an embodiment of the present invention.

In one embodiment of the present invention, the diagnostic information is received from a medical imaging device that is provided on the surgical instrument. The diagnostic information may contain spatial location of each of a plurality of physiological or anatomical features of the patient. In the example which the surgical instrument is the epidural needle, the navigation module 100 may determine the best path for performing epidural needle insertion based on the diagnostic information; and the navigation module 100 defines the navigation landmarks based on the best path for performing epidural needle insertion. In order to obtain accurate and un-distorted diagnostic information, it is preferred that the medical imaging device performs real-time image capturing at a location as close to the site of epidural needle insertion as possible. With reference to FIG. 11, to resolve this issue, the medical imaging device 50 may be coaxially provided in proximity to the insertion portion 40 (i.e., the epidural needle) of the surgical instrument. Furthermore, since the patient may not be static at all times (e.g., the patient may change his/her body posture), the medical imaging device 50 have to update diagnostic information related of the patient in real time; therefore, the spatial coordinates corresponding to the position of the navigation landmarks are configured in real-time accordingly. Meanwhile, the medical imaging device 50 and/or the navigation module 100 may provide real-time information related to the spatial deviation of the alignment reference points relative to the navigation landmarks.

In some embodiments of the present invention, the surgical instrument may further comprise an orientation detection module 60 (with reference to FIG. 10) for determining the orientation of the surgical instrument relative to the real space. The orientation detection module 60 then provides the orientation data of the surgical instrument to the navigation module 100 for determining the spatial deviation of the alignment reference points relative to the navigation landmarks. As an example, the orientation detection module 60 may be a gyroscope. The surgical instrument may also comprise a penetration depth detection module for determining a depth of penetration of the surgical instrument into the patient. As an example, the depth detection module may be a pressure sensor or optical sensor. The penetration depth detection module may help detecting the position of the surgical instrument in the 3-dimensional coordinate system in real space for determining whether the surgical instrument has reached the appropriate penetration depth relative to the surface of the surgical target (e.g., the skin of the patient).

The following are exemplary embodiments which demonstrate the actual implementation on epidural anesthesia using the augmented reality assisted system in accordance with the present invention. In these embodiments, the epidural needle comprises an insertion portion for inserting into the patient; and the medical imaging device is coaxially provided in proximity to the insertion portion.

In the first embodiment, epidural anesthesia may comprise the following steps:
(1) The epidural needle is in a retraction mode. The epidural needle comprising the medical imaging device can be moved over to a region of the skin of the patient to obtain the 3D image data (diagnostic information) of the anatomy from the medical imaging device (e.g., an annular ultrasound transducers or 3D ultrasound) and to build a 3D model of the anatomy of the patient.
(2) Building the 3D model of anatomy of the patient.
(3) Determining the proper position and angle (or orientation) for insertion of the epidural needle in 3D real space. The position and angle are displayed to the medical practitioner via the head wearable device.
(4) The medical practitioner can align the epidural needle to the projected virtual image of the epidural needle in space by the head wearable device for navigation.
(5) The central epidural needle is inserted by hands or an automatic pressing device. During the insertion, the depth of the epidural needle is monitored by a medical imaging device (e.g., a front ultrasound transducer near the tip of the epidural needle). The central epidural needle is removed after the specified depth is reached.
(6) Attach the syringe to the epidural needle. Push the entire epidural needle deeper until the it detects the loss of the resistance by pressure sensor or light sensor.

In the second embodiment, epidural anesthesia may comprise the following steps:
(1) Using medical imaging device (e.g., 3D ultrasound scanning) to scan a region of the skin of the patient to obtain 3D image data of the anatomy and build the 3D model of the patient.
(2) Determining the proper position and angle (or orientation) for insertion of the epidural needle in 3D real space. The position and angle are displayed to the medical practitioner via the head wearable device. The medical practitioner can use the head wearable device to check the epidural needle path from the simulated results.
(3) The head wearable device projects a virtual image of the epidural needle at the preferred insertion position on the skin having the preferred angle of insertion according to the result of Step (2).
(4) The medical practitioner can align the epidural needle to the virtual image of the epidural needle in 3D space projected by the head wearable device.
(5) The central epidural needle is inserted by hands or an automatic pressing device. During the insertion, the depth of the epidural needle is monitored by the medical imaging device (e.g., a front ultrasound transducer near the tip of the epidural needle). The central epidural needle is removed after the specified region is reached.
(6) Attach the syringe to the epidural needle. Push the entire epidural needle deeper until the it detects the loss of the resistance by pressure sensor or light sensor.

In the third embodiment, epidural anesthesia may comprise the following steps:
(1) Using medical imaging device (e.g., 3D ultrasound scanning) to scan a region of the skin of the patient to obtain 3D image data of the anatomy and build the 3D model of the patient.
(2) Determining the proper position and angle (or orientation) for insertion of the epidural needle in 3D real space. The position and angle are displayed to the medical practitioner via the head wearable device. The medical practitioner can use the head wearable device to check the epidural needle path from the simulated results.
(3) Remove the medical imaging device away. The head wearable device projects a virtual image of the epidural needle at the preferred insertion position on the skin having the preferred angle of insertion according to the result of Step (2).
(4) The medical practitioner can align the epidural needle to the virtual image of the epidural needle in 3D space projected by the head wearable device.
(5) The central epidural needle is inserted by hands or an automatic pressing device. During the insertion, the depth of the epidural needle is monitored by the medical imaging device (e.g., a front ultrasound transducer near the tip of the epidural needle). The central epidural needle is removed after the specified region is reached.
(6) Attach the syringe to the epidural needle. Push the entire epidural needle deeper until the it detects the loss of the resistance by pressure sensor or light sensor.

The foregoing description of embodiments is provided to enable any person skilled in the art to make and use the subject matter. Various modifications to these embodiments will be readily apparent to those skilled in the art, and the novel principles and subject matter disclosed herein may be applied to other embodiments without the use of the innovative faculty. The claimed subject matter set forth in the claims is not intended to be limited to the embodiments shown herein but is to be accorded the widest scope consistent with the principles and novel features disclosed herein. It is contemplated that additional embodiments are within the spirit and true scope of the disclosed subject matter. Thus, it is intended that the present invention covers modifications and variations that come within the scope of the appended claims and their equivalents.

What is claimed is:

1. An augmented reality system for real space navigation, comprising:
a navigation module, for determining a set of spatial coordinates corresponding a position in a three dimensional real space for each of a plurality of navigation landmarks, the plurality of navigation landmarks corresponding to target locations or target orientations of a task subject in the three dimensional real space for performing a task; and
a virtual image display module for displaying a virtual image correlated to one of the plurality of navigation landmarks such that the virtual image is perceived by a user to be at the position in the three dimensional real space, the virtual image being composed of a plurality of binocular pixels, each of the plurality of binocular pixels is formed by a first light signal being directed to a first retina of the user and a second light signal being directed to a second retina of the user;
wherein each of the first light signal is respectively directed with a first angle to a specific unit area before entering the first eye and each of the second light signal is respectively directed with a second angle to a specific unit area before entering the second eye,
wherein a depth coordinate perceived by the user in the real space of each of the plurality of binocular pixels having a specific horizontal coordinate and vertical coordinate is rendered by projecting the first light signal and the second light signal corresponding to the binocular pixel to a specific pair of designated locations on surface of the first retina and the second retina that is specific for perception of the horizontal coordinate, the vertical coordinate, and the depth coordinate in real space,
wherein the specific unit area and the first angle associated with the first light signal correspond to a first specific spatial area on the first retina such that the first light signal directed to the unit area with the first angle is received by the first specific spatial area on the first retina, the specific unit area and the second angle associated with the second light signal correspond to a second specific spatial area on the second retina such that the second light signal directed to the unit area with the second angle is received by the second specific spatial area on the second retina, the specific pair of designated locations are consisted of the first specific spatial area on the first retina, and the second specific spatial area on the second retina,
wherein the first angle and the second angle are in consistence with a convergence angle between the first eye and the second eye when the user fixate at the virtual image, the depth coordinate perceived by the viewer of the virtual image correlate to intersection of light path extension of the first light signal and the second light signal,
wherein the binocular pixels of the virtual image have various depth coordinates, the virtual image is rendered with specific orientation or coordinate in real space for navigating the user for performing the task.

2. The augmented reality system for real space navigation of claim 1, wherein the first light signal and the second light signal are directed to the pair of designated locations with nonspecific incident angle respectively for the user to perceive the depth coordinate regardless a projection angle of the first light signal onto the first retina and a projection angle of the second light signal onto the second retina.

3. The augmented reality system for real space navigation of claim 1, wherein the pair of designated locations comprises a first designated location and a second designated location, the first designated location has a fixed relative position on the first retina and the second designated location has a fixed relative position on the second retina.

4. The augmented reality system for real space navigation of claim 3, wherein a variation in the depth coordinate of each of the plurality of binocular pixel perceived by the user is rendered by changing a relative distance between the first designated location and the second designated location.

5. The augmented reality system for real space navigation of claim 1, wherein the vertical coordinate or the horizontal coordinate perceived by the user in the real space of the plurality of binocular pixel of the virtual image are rendered by projecting the first light signal and the second light signal to a pair of designated locations on surface of the first retina and the second retina having vertical positions or horizontal position corresponding to the vertical coordinate or the horizontal coordinate regardless the projection angle of the first light signal onto the first retina and the projection angle of the second light signal onto the second retina.

6. The augmented reality system for real space navigation of claim 1, wherein a plurality of alignment reference points are assigned to the task subject, a position of each of the plurality of alignment references points are determined by navigation module.

7. The augmented reality system for real space navigation of claim 6, wherein the navigation module respectively determines a spatial deviation of one of the plurality of alignment reference points relative to one of the plurality of navigation landmarks.

8. An augmented reality assisted system for performing a medical procedure on a patient, comprising:
a navigation module, for determining a set of spatial coordinates corresponding a position in a three dimensional real space for each of a plurality of navigation landmarks based on a diagnostic information of a patient, the plurality of navigation landmarks corresponding to target locations or target orientations of a surgical instrument in the three dimensional real space for performing the medical procedure; and
a virtual image display module for displaying a virtual image correlated to one of the plurality of navigation landmarks such that the virtual image is perceived by a user to be at the position in the three dimensional real space, the virtual image being composed of a plurality of binocular pixels, each of the plurality of binocular pixels is formed by a first light signal being directed to a first retina of the user and a second light signal being directed to a second retina of the user;
wherein each of the first light signal is respectively directed with a first angle to a specific unit area before entering the first eye and each of the second light signal is respectively directed with a second angle to a specific unit area before entering the second eye,
wherein a depth coordinate perceived by the user in the real space of each of the plurality of binocular pixels having a specific horizontal coordinate and vertical coordinate is rendered by projecting the first light signal and the second light signal corresponding to the binocular pixel to a specific pair of designated locations on surface of the first retina and the second retina that is specific for perception of the horizontal coordinate, the vertical coordinate, and the depth coordinate in real space,
wherein the specific unit area and the first angle associated with the first light signal correspond to a first specific spatial area on the first retina such that the first light signal directed through the unit area with the first angle is received by the first specific spatial area on the first retina, the specific unit area and the second angle associated with the second light signal correspond to a second specific spatial area on the second retina such that the second light signal directed through the unit area with the second angle is received by the second specific spatial area on the second retina, the specific pair of designated locations are consisted of the first specific spatial area on the first retina, and the second specific spatial area on the second retina,
wherein the first angle and the second angle are in consistence with a convergence angle between the first eye and the second eye when the user fixate at the virtual image, the depth coordinate perceived by the viewer of the virtual image correlate to intersection of light path extension of the first light signal and the second light signal,
wherein the binocular pixels of the virtual image have various depth coordinates.

9. The augmented reality assisted system of claim 8, wherein the first light signal and the second light signal are directed to the pair of designated locations with nonspecific incident angle respectively for the user to perceive the depth coordinate regardless a projection angle of the first light signal onto the first retina and a projection angle of the second light signal onto the second retina.

10. The augmented reality assisted system of claim 9, wherein the pair of designated locations comprises a first designated location and a second designated location, the first designated location has a fixed relative position on the first retina and the second designated location has a fixed relative position on the second retina.

11. The augmented reality assisted system of claim 10, wherein a variation in the depth coordinate of each of the plurality of binocular pixels perceived by the user is rendered by changing a relative distance between the first designated location and the second designated location.

12. The augmented reality system for real space navigation of claim 8, wherein the virtual image display module is a head wearable device, the set of spatial coordinates, the depth coordinate, the horizontal coordinate, and the vertical coordinate are measured with respect to a location of the head wearable device.

13. The augmented reality assisted system of claim 8, wherein the vertical coordinate or the horizontal coordinate perceived by the user in the real space of the plurality of binocular pixel of the virtual image are rendered by projecting the first light signal and the second light signal to a pair of designated locations on surface of the first retina and the second retina having vertical positions or horizontal position corresponding to the vertical coordinate or the horizontal coordinate regardless the projection angle of the first light signal onto the first retina and the projection angle of the second light signal onto the second retina.

14. The augmented reality assisted system of claim 8, wherein a plurality of alignment reference points are assigned to the surgical instrument, a position of each of the plurality of alignment references points are determined by navigation module.

15. The augmented reality assisted system of claim 14, wherein the navigation module respectively determines a spatial deviation of one of the plurality of alignment reference points relative to one of the plurality of navigation landmarks.

16. The augmented reality assisted system of claim 15, wherein the virtual image module output a visual cue to the user when the spatial deviation is larger than a first predetermined value or smaller than a second predetermined value.

17. The augmented reality assisted system of claim 8, wherein the medical imaging device provides a real-time information related to the patient, the set of spatial coordinates corresponding the position in a three dimensional real space for each of a plurality of navigation landmarks is configured according to the real time information.

18. The augmented reality assisted system of claim 8, wherein the navigation module is provided on the virtual image display module, or the navigation module is an indoor positioning system provided separately to the virtual image display module.

19. The augmented reality assisted system of claim 8, wherein one of the plurality of navigation landmarks correlates to a location for performing medical procedure on the target object.

20. The augmented reality assisted system of claim 8, wherein the medical imaging device provides a real-time information related to a spatial deviation of one of the plurality of alignment reference points relative to one of the plurality of navigation landmarks.

* * * * *